549-321 SR
4/7/87 OR H 000,253

United States Statutory Invention Registration [19]

[11] Reg. Number: H253

Sitzmann et al. [43] Published: Apr. 7, 1987

[54] BRANCH CHAINED POLYNITRODIOLS

[75] Inventors: Michael E. Sitzmann, Adelphi; William H. Gilligan, Ft. Washington, both of Md.

[73] Assignee: The United States of America as represented by the Secretary of the Navy, Washington, D.C.

[21] Appl. No.: 875,159

[22] Filed: Jun. 17, 1986

[51] Int. Cl.[4] ..... C07D 307/28; C07D 307/26

[52] U.S. Cl. ..... 549/321; 568/844; 568/853

*Primary Examiner*—John F. Terapane
*Assistant Examiner*—Susan Wolffe
*Attorney, Agent, or Firm*—Kenneth E. Walden; Roger D. Johnson

[57] ABSTRACT

Energetic branched polynitrodiols of the formula

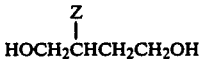

wherein Z is $—C(NO_2)_3$, $—CF(NO_2)_2$, $—C(NO_2)_2CH_3$, or $—N(NO_2)CH_3$, and a method of preparation. These diols are useful as components of energetic binders for plastic-bonded explosives.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BRANCH CHAINED POLYNITRODIOLS

BACKGROUND OF THE INVENTION

This invention relates to alcohols and more particularly to energetic polynitroakyldiols.

The chief promise of energetic polynitrodiols for practical explosive applications are as monomers for the synthesis of hydroxy termined prepolymers. In practice, the prepolymers are mixed with a solid explosive, $$HOCH_2 \ldots CH_2OH + X_2RHO[CH_2 \ldots CH_2ORO-CH_2 \ldots CH_2]_nOH$$

ex., RDX or HMX, an energetic plasticizer and isocyanate curing agents. The liquid slurry is then cast into a suitable mold and cured to form a rubbery matrix which not only binds the solid explosive and defines the shape, but also contributes energy to the final composition.

The most attractive diols from the standpoint of energy and availability are 2,2-dinitro-1,3-propanediol (A-diol) and 2,2,8,8-tetranitro-4,6-dioxa-1,9-nonanediol (DINOL). Both of these diols, as is the case with the majority of known polynitromonols, are substituted with nitro groups in the beta-position. Alcohols of this type are easily prepared by the addition of the respective nitrocarbanion to formaldehyde (Henry reaction). Unfortunately, however,

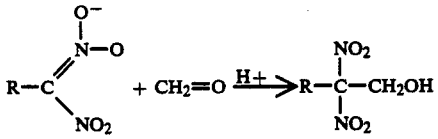

this reaction is reversible in the presence of even mild bases and the resultant nitrocarbanion is subject to side reactions and decomposition over

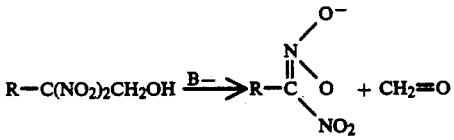

varying periods of time.

Energetic polymers that contain unreacted beta-nitro alcohol end groups are also subject to the reverse Henry reaction and under the conditions of isocyanate curing wherein basic urethane linkages are formed, decomposition can and does occur. This leads to poor thermal stability and aging characteristics. This is undoubtedly the reason why AFNOL, an energetic polymer, formed from pimeloyl chloride and DINOL was ultimately rejected as a candidate energetic polymer.

For this reason, a considerable effort has been expended among different groups to prepare energetic diols that are not subject to deformylation under basic conditions. These have been without exception straight chain diols, which generally, though not always, contain both nitramine and gem dinitro groups on the backbone. These structural characteristics lead to hard prepolymers with poor solubilities in the energetic plasticizers used in the explosive compositions. This type of diol appears to be of limited usefulness.

SUMMARY OF THE INVENTION

Accordingly, an object of this invention is to provide new energetic polynitrodiols.

Another object of this invention is to provide new polynitrodiols which are useful as components of energetic polymers.

A further object of this invention is to provide new polynitrodiols which are stable to deformylation (loss of formaldehyde).

Yet another object of this invention is to provide new branched chain polynitrodiols which can improve the hydrolytic stability of energetic polymers such as polyesters.

A still further object of this invention is to provide a method of preparing these new energetic polynitrodiols.

These and other objects of this invention are achieved by providing branched polynitrodiols of the formula

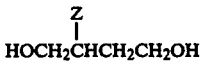

wherein Z is $-C(NO_2)_3$, $-CF(NO_2)_2$, $-C(NO_2)_2CH_3$, or $-N(NO_2)CH_3$. These branched polynitrodiols may be prepared by the following method:

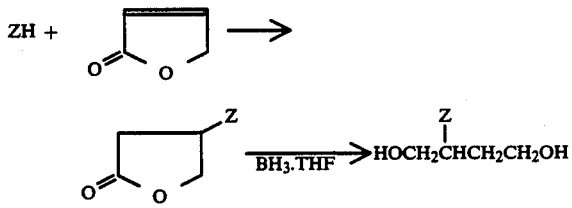

wherein Z is as defined above.

DETAILED DESCRIPTION OF THE PREFERRED EMBODIMENT

The energetic branched polynitroakyldiols of this invention are 2-(trinitromethyl)-1,4-butanediol, $HOCH_2CH[C(NO_2)_3]CH_2CH_2OH$; 2-(fluorodinitromethyl)-1,4-butanediol, $HOCH_2CH[CF(NO_2)_2]CH_2CH_2OH$; 2-(1,1-dinitroethyl)-1,4-butanediol, $HOCH_2CH[C(NO_2)_2CH_3]CH_2CH_2OH$; and 2-(methylnitraza)-1,4-butanediol, $HOCH_2CH[N(NO_2)CH_3]CH_2CH_2OH$. These diols can be used as monomers to produce energetic polymeric binders for use in plastic-bonded explosives.

These energetic branched polynitroalkyldiols offer advantages over prior art diols such as 2,2-dinitropropane-1,3-diol(A-diol), $C(NO_2)_2[CH_2OH]_2$, and 4,6-dioxa-2,2,8,8-tetranitrononane-1,9-diol (DINOL), $CH_2[OCH_2C(NO_2)_2CH_2OH]_2$, in the production of energetic polymeric binders. These branched polynitroalkyldiols produce polymers with end groups which do not undergo deformylation.

Another important feature of these diols is that the number of atoms in the backbone is large enough to inhibit ring formation yet, short enough so that a large number of oxygen linkages will be incorporated in the backbone of the resultant polymer. These divalent oxygen linkages add flexibility to the polymer backbone and markedly enhance physical properties. Moreover, the fact the energetic groups are carried on branches is important from the standpoint of physical properties since nitroamino or gem-dinitro groups on the backbone of a prepolymer can markedly lower physical properties.

The reaction sequences for preparing these branched polynitroalkyl diols can be summarized as follows:

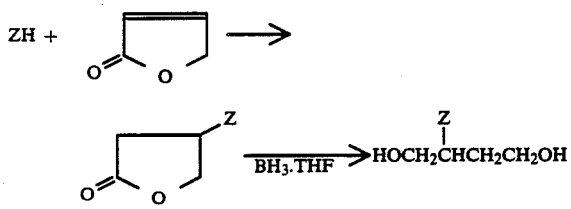

where Z is $—C(NO_2)_3$, $—CF(NO_2)_2$, $—C(NO_2)_2CH_3$, or $—N(NO_2)CH_3$. The reaction of one mole of trinitromethane with one mole of gamma-crotonolactone under the reaction conditions of example 1 produces 4-hydroxy-3-(trinitromethyl)butyric acid, gamma-lactone which is reduced by borane-tetrahydrofuran to produce 2-(trinitromethyl)-1,4-butanediol as shown in example 3. Similarly, the reaction of one mole of fluorodinitromethane with gamma-crotonolactone under the reaction conditions of example 2 produces 4-hydroxy-3-(fluorodinitromethyl)butric acid, gamma-lactone which is reduced by borane-tetrahydrofuran to produce 2-(fluorodinitromethyl)-1,4-butanediol as shown in example 4. Using the same procedure, 1,1-dinitroethane and gamma-crotonolactone can be used to produce 2-(1,1-dinitroethyl)-1,4-butanediol and methyl nitramine and gamma-crotonolactone can be used to produce 2-(methylnitraza)-1,4-butanediol.

The general nature of the invention having been set forth, the following examples are presented as specific illustrations thereof. It will be understood that the invention is not limited to these examples but is susceptible to various modifications that will be recognized by one skilled in the art.

The gamma-crotonolactone starting material used in these examples was prepared by the procedure disclosed by S. Takano and K. Ogasawara in *Synthesis*, 1974, (1), p. 42.

EXAMPLE 1

4-Hydroxy-3-(trinitromethyl)butyric acid, gamma-lactone

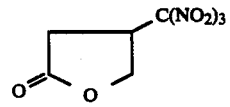

A mixture of 7.5 g (0.089 mole) of gamma-crotonolactone, 56.7 g (0.124 mole) of 33% aqueous nitroform and 32 ml of methanol was stirred in an oil bath at 72°–75° C. for 5 hr. The mixture was then cooled in an ice bath to precipitate an oil which turned to a solid and was removed by filtration and washed with cold water to give 13.7 g, mp 103°–105° C. The water wash precipitated more oil from the filtrate. After extraction into methylene chloride, the oil was crystallyzed from methanol-water to give an additional 1.55 g of product [total yield of 15.25 g (73%)]. Recrystallization from methanol-water raised the mp to 105°–106° C.; $^1H$ NMR($CD_2Cl_2$): 2.74–3.36 (m,2H); 4.25–4.60 (m, 2H); 4.75–4.97 (m, 1H); IR (KBr): 1775 (shoulder at 1787) (C=0); 1600, 1590 ($NO_2$) $cm^{-1}$.

Anal. Calcd for $C_5H_5N_3O_8$: C, 25.54; H, 2.14; N, 17.87. Found: C, 25.63; H, 2.13; N, 17.81.

EXAMPLE 2

4-Hydroxy-3-(fluorodinitromethyl)butyric acid, gamma-lactone

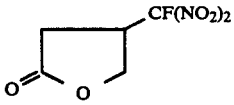

A solution containing 16.5 g (0.196 mole) of gamma-crotonolactone and 31.8 g (0.256 mole) of fluorodinitromethane in 100 ml of methylene chloride (protected by a drierite drying tube) was stirred in an ice bath while 30.8 ml of pyridine was added in 3 ml portions over 5 min. The solution was stirred at ice bath temperature for 3 hr. before an additional 8.9 ml of pyridine was added in 3 portions over 2 min. After an additional 3 hr. at 0° C., the solution was poured into a solution containing 85 ml conc. hydrochloric acid diluted with 170 ml of water. The mixture was stirred vigorously at ambient temperature for 15 min. before the methylene chloride layer was separated, washed with water and dried over sodium sulfate. Removal of the methylene chloride gave 28.4 g of tan solid which was dissolved in 120 ml of hot chloroform. The hot solution was stirred with 10 g of silica gel 60, then filtered and the silica gel was washed with 120 ml of hot chloroform. Hexane was added to the filtrate (at room temperature) to the cloud point. Cooling to −15° C. gave 21.9 g of white crystals, mp 58°–60° C. A second crop (4.6 g, mp 57°–59° C.) raised the yield to 26.5 g (65%); $^1H$ NMR ($CDCl_3$): 2.55–3.14 (m, 2H); 3.97–4.88 (m, 3H); IR(KBr): 1800, 1766 (C=0), 1609, 1600 (shoulder) ($NO_2$) $cm^{-1}$.

Anal. Calcd for $C_5H_5N_2FO_6$: C, 28.86; H, 2.42; N, 13.46; F, 9.13. Found: C, 28.95; H, 2.45; N, 13.18; F, 9.12.

EXAMPLE 3

2-(Trinitromethyl)-1,4-butanediol

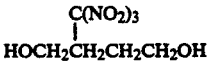

A 1M solution of borane-THF (10 ML, 10 mmole) was stirred under a nitrogen atmosphere in a cold water bath (15° C.) while 2.1 g (8.94 mmole) of 4-hydroxy-3-(trinitromethyl)butyric acid, gamma-lactone was added. The solution was stirred at 25° C. for 1 hr. and then at 35°–37° C. for 3 days before it was cooled to room temperature and 1 ml of water was slowly added dropwise. Most of the THF was removed and the residue was stirred with ether. The insoluble material (boric acid) was removed by filtration and the ether filtrate was extracted twice with water to remove remaining boric acid. The ether was removed to give 2.10 g (98%) of an oil which was essentially pure by TLC. An analytical sample was obtained by chromatography on silica gel 60 with methylene chloride-acetone (80/20) as eluent: $^1H$ NMR ($CD_2Cl_2$) 1.90–2.12 (m, 2H), 2.44 (broad OH), 3.60 (broad m, 1H), 3.93 (t, 2H), 4.23 (d, 2H); IR (film) 3700–3050 (OH), 1600 ($NO_2$) $cm^{-1}$.

Anal. Calcd for $C_5H_9N_3O_8$: C, 25.11; H, 3.79; N, 17.57. Found C, 25.00; H, 3.86; N, 17.34.

EXAMPLE 4

2-(Fluorodinitromethyl)-1,4-butanediol

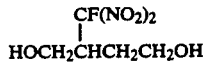

To a 1M solution of borane-THF (5 ml, 5 mmole) stirred under a nitrogen atmosphere in an ice bath was added 1.0 g (4.8 mmole) of 4-hydroxy-3-(fluorodinitromethyl)butyric acid, gamma-lactone. The solution was then held in a water bath at 25°-28° C. for 24 hr. before 1 ml of water was slowly added dropwise. The solution was poured into 15 ml of water and extracted with ether to give 1.02 g (100%) of an oil which was essentially pure by TLC. Chromatography on silica gel 60 using methylene chloride-acetone (80/20) as eluent gave an analytical sample. $^1H$ NMR ($CDCl_3$) 1.70–1.93 (m, 2H), 2.36(OH), 3.34–3.97 (m, 5H); IR (film) 3700–3050 (OH), 1605 ($NO_2$) $cm^{-1}$.

Anal Calcd for $C_5H_9N_2FO_6$: C, 28.31; N, 4.28; N, 13.21: F, 8.96. Found: C, 28.04; H, 4.44; N, 12.81; F, 8.50.

Obviously many numerous modifications and variations of this invention are possible in light of the above teachings. It is therefore to be understood that within the scope of the appended claims the invention may be practiced otherwise than as specifically described.

What is claimed is:

1. A diol of the formula

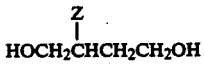

wherein Z is selected from the group consisting of —C($NO_2$)$_3$, —CF($NO_2$)$_2$, —C($NO_2$)$_2$$CH_3$, and —N($NO_2$)$CH_3$.

2. The diol of claim 1 which is 2-(trinitromethyl)-1,4-butanediol.

3. The diol of claim 1 which is 2-(fluorodinitromethyl)-1,4-butanediol.

4. The diol of claim 1 which is 2-(1,1-dinitroethyl)-1,4-butanediol.

5. The diol of claim 1 which is 2-(methylnitraza)-1,4-butanediol.

6. A lactone of the formula

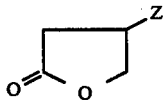

wherein Z is selected from the group consisting of —C($NO_2$)$_3$ —CF($NO_2$)$_2$, —C($NO_2$)$_2$$CH_3$, and —N($NO_2$)$CH_3$.

7. The lactone of claim 6 wherein Z is —C($NO_2$)$_3$.

8. The lactone of claim 6 wherein Z is —CF($NO_2$)$_2$.

9. The lactone of claim 6 wherein Z is —C($NO_2$)$_2$$CH_3$.

10. The lactone of claim 6 wherein Z is —N($NO_2$)$CH_3$.

11. A process for preparing a branched polynitrodiol comprising the following steps in order:

(1) reacting one mole of a compound of the formula Z—H with one mole of gamma-crotonolactone to produce a lactone of the formula

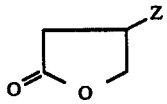

(2) reducing the lactone produced in step (1) with borane-tetrahydrofuran to produce the desired branched polynitrodiol of the formula

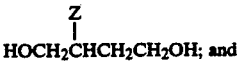

(3) isolating the product branched polynitrodiol; wherein Z is selected from the group consisting of —C($NO_2$)$_3$, —CF($NO_2$)$_2$, —C($NO_2$)$_2$$CH_3$, and —N($NO_2$)$CH_3$.

* * * * *